United States Patent [19]

Frincke et al.

[11] Patent Number: 5,004,606

[45] Date of Patent: Apr. 2, 1991

[54] NON-COVALENT ANTIBODY-ANTHRACYCLINE IMMUNOCOMPLEXES

[75] Inventors: James M. Frincke, Olivenhain; Richard M. Bartholomew, San Diego; Robert O. Dillman, Solana Beach, all of Calif.

[73] Assignee: Hybritech Incorporated, San Diego, Calif.

[21] Appl. No.: 911,269

[22] Filed: Sep. 24, 1986

[51] Int. Cl.$^5$ .................... A61K 37/00; A61K 39/00
[52] U.S. Cl. ................ 424/85.8; 424/85.91; 424/86; 424/87; 424/88; 530/387; 530/388; 530/389; 514/2; 514/885
[58] Field of Search .................... 424/85–88, 424/85.8, 85.91; 530/387–389; 514/885, 2

[56] References Cited

U.S. PATENT DOCUMENTS

| 4,093,607 | 6/1978 | Sela et al. | 424/85 |
| 4,263,279 | 4/1981 | Sela et al. | 424/85 |
| 4,401,592 | 8/1983 | Yoshikumi et al. | 424/85 |
| 4,520,226 | 5/1985 | Neville et al. | 424/85 |
| 4,671,958 | 6/1987 | Rodwell et al. | 530/391 |

OTHER PUBLICATIONS

Zaharko et al, *Methods in Cancer Res.*, XVI, 1979, pp. 347–380.
Hurwitz et al, *Int. J. Cancer* 21, 1978, pp. 747–755.
Thorpe, Monoclonal Antibodies, 1985; ed. Pinchera et al, pp. 475–506.
Ghose et al, *Methods in Enzymology*, vol. 93, 1983, pp. 280–333.
Hurwitz et al, J Applied Biochem. 1980 (2), pp. 25–35.
Suzuki et al, *Chem Pharm. Bull.*, 29(3), 1981, pp. 844–848.
Rowland et al, Monoclonal Antibodies for Cancer Detection and Therapy, 1985, ed. Baldeuin et al, Chapter 17, pp. 345–364.
Sullivan et al, *PNAS* 1986, pp. 6117–6121.
Denei et al, *Science,* 1986, pp. 148–150.
Webbs et al, CA, vol. 104, 1986, #199671p.
Site-Specific Drug Delivery, ed. Tomlinson et al, 1986, pp. 93–110, (Davis et al.).
Monoclonal Antibodies and Cancer Therapy, ed. Reisfeld et al, 1985, pp. 243–256, Arnon, et al.
Hurwitz, et al., Int. J. Cancer, 21, 747 (1978).

*Primary Examiner*—Garnette D. Drarer
*Attorney, Agent, or Firm*—Theresa A. Brown; Ronni L. Sherman; Paul C. Steinhardt

[57] ABSTRACT

A composition comprising a non-covalent immunocomplex of an anthracycline agent and an antibody selected to bind a target antigen and enhance the cytotoxicity of the anthracycline agent is disclosed. In accordance with the invention, the efficacy of an anthracycline as an anti-tumor agent for use in in vivo therapy is enhanced by administering to a patient a non-covalent immunocomplex provided herein.

14 Claims, 6 Drawing Sheets

NON-COVALENT ANTIBODY-ANTHRACYCLINE IMMUNOCOMPLEXES

FIELD OF THE INVENTION

This invention relates generally to non-covalent immunocomplexes for use in in vivo therapy. More particularly, it relates to non-covalent immunocomplexes comprising monoclonal antibodies and anthracycline agents for use in the treatment of cancer and other disease states.

BACKGROUND

Developments in hybridoma technology have opened new avenues for the treatment of cancer and other disease states. For purposes of in vivo therapy, monoclonal antibodies having specificity for an in vivo target, such as tumor tissue, have been administered alone with direct cytotoxic effect. Alternatively, monoclonal antibody conjugates comprising cytotoxic agents, such as drugs, toxins or radioisotopes covalently bound to monoclonal antibodies have been administered to mediate the selective delivery of such agents to a tumor target. However, reported trials of monoclonal antibodies administered alone have yielded inconsistent results. While transient anti-tumor effects have been observed in several studies, desirable complete remissions have generally not resulted. In vivo trials with monoclonal antibody conjugates of drugs, toxins or radioisotopes are still in the early developmental stages.

Anthracycline compounds and their derivatives have generally proven useful as anti-tumor agents in the treatment of cancer, including lymphomas, leukemias, sarcomas and cancers of the breast and lung. Among the anthracyclines most useful as anti-tumor agents are doxorubicin and daunorubicin. Doxorubicin, one of the most commonly used chemotherapeutic agents, displays activity against a wide range of human neoplasms. Doxorubicin is effective in the treatment of acute leukemias and malignant lymphomas and has been administered as a single agent, or in combination with other agents to treat, for example, chronic lymphocytic leukemia ("CLL") or cutaneous T-cell lymphoma ("CTCL"). Additionally, doxorubicin is a valuable component of various regimens of chemotherapy for carcinomas of the breast and lung, and is beneficial in the treatment of a wide range of sarcomas. By comparison, daunorubicin is very useful in the treatment of acute lymphocytic and acute granulocytic leukemias.

Antibody conjugates comprising anthracycline agents covalently attached to antibodies have been prepared using a variety of techniques. One such technique employs dextran to provide covalent linkages between the antibody and the anthracycline agent, e.g. doxorubicin. It has been extremely difficult, however, to prepare effective conjugates comprising anthracyclines and antibodies. Significantly, the size of such conjugates results in rapid clearance by the reticuloendothelial system. Additional limitations inherent in the use of such conjugates include the need for modification of the anthracycline agent prior to covalent attachment to the antibody, usually resulting in decreased potency, and the need for metabolic cleavage of the agent from the antibody to produce the desired cytotoxic effect at the in vivo target. Further, conjugation may impair the immunoreactivity and alter the biodistribution of the antibody, usually resulting in decreased concentration at the target tissue, and may increase immunogenicity.

The problems enumerated in the foregoing are not intended to be exhaustive, but are among many which tend to limit the clinical value of antibody conjugates of anthracyclines as anti-tumor agents. Accordingly, while the selective delivery of anthracycline agents to an in vivo target may be accomplished, there continues to exist a need to enhance the cytotoxic efficacy of anthracycline at the target tissue.

SUMMARY OF THE INVENTION

The present invention provides a composition for use in in vivo therapy comprising a non-covalent immunocomplex of an anthracycline agent and an antibody selected to bind a target antigen and enhance the cytotoxicity of the anthracycline agent. The anthracycline agent may be selected from the group consisting of doxorubicin, daunorubicin, epirubicin, N-trifluoroacetyl doxorubicin-14-valerate, aclacinomycin, morpholinodoxorubicins, and derivatives thereof. Preferably, the antibody is a monoclonal antibody selected to bind a tumor-associated antigen, such as an antigen associated with chronic lymphocytic leukemia, cutaneous T-cell lymphoma, or other T-cell neoplasm.

In accordance with the invention, a composition comprising a non-covalent immunocomplex may be prepared by mixing an anthracycline agent in solution and an antibody selected to bind a target antigen and enhance the cytoxicity of the anthracycline agent.

Further in accordance with the present invention, the efficacy of an anthracycline as an anti-tumor agent for use in in vivo therapy may be enhanced by administering to a patient a composition comprising a non-covalent immunocomplex described herein.

The present invention has been summarized in order that the detailed description that follows and the contribution to the art may be better appreciated.

DETAILED DESCRIPTION OF THE INVENTION

Figure 1A:
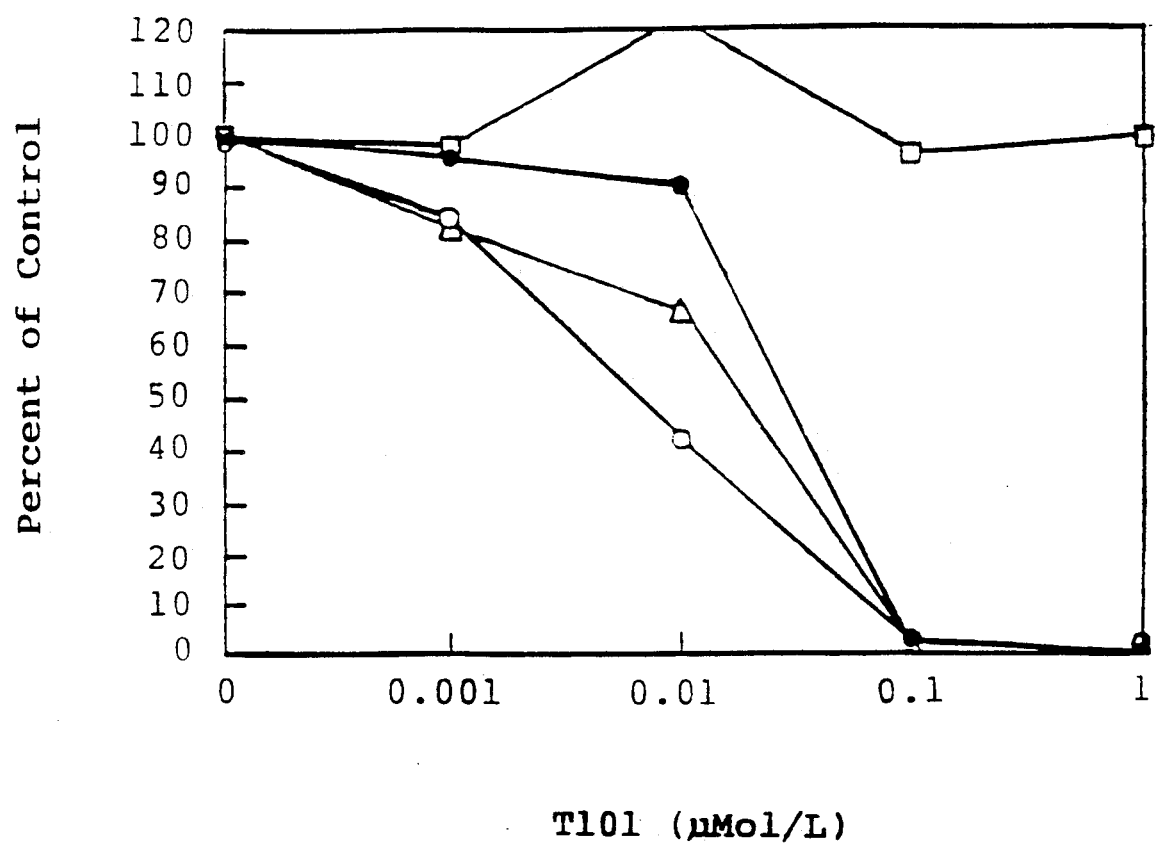
FIG. 1(A–C) provides graphs for comparison of the cytotoxicity of antibody conjugates, the T101-DOX immunocomplex of the invention, and a control, as measured by $^3$H-TdR uptake.

As indicated above, the present invention in one aspect, provides a composition comprising a non-covalent immunocomplex of an anthracycline agent and an antibody selected to bind a target antigen and enhance the cytotoxicity of the anthracycline agent.

The present invention, in another aspect, is predicated upon the unexpected discovery that the cytotoxic efficacy of an athracycline as an anti-tumor agent for use in in vivo therapy is enhanced by administering to a patient a composition comprising a non-covalent immunocomplex described herein Administration of an immunocomplex of the invention may be accomplished intravenously, intraperitoneally, subcutaneously, intralymphatically or intracranially.

In accordance with the invention, a composition comprising such an immunocomplex may be prepared by mixing an anthracycline agent in solution and an antibody selected to bind a target antigen and enhance the cytotoxicity of the anthracycline agent. The non-covalent complexation of an anthracycline agent and an antibody is accomplished by such molecular mechanisms as ion exchange and hydrophobic bonding. As anthracycline agents have limited solubility in aqueous systems, such agents tend to partition into lipophilic regions in solution and are, therefore, capable of "binding" or associating through hydrophobic interaction with lipophilic regions of an antibody molecule.

Equilibrium dialysis may be used to confirm that a non-covalent complex, in accordance with the present invention, has been formed and to assess the ratio of anthracycline molecules bound to antibody to unbound anthracycline molecules. Optical density measurements may be used to determine the number of anthracycline molecules bound per antibody. As the number of anthracycline molecules per antibody molecule increases beyond an optimum threshold of antibody solubility, the antibody-anthracycline complex will begin to precipitate in aqueous buffered solution. This will tend to impair the administration of such a solution to a patient for use in in vivo therapy. Additionally, it is important to note that the number of anthracycline molecules bound to a given antibody molecule affects the in vivo pharmacokinetics and biodistribution of an antibody-anthracycline complex, which may affect the potency and overall efficacy of such a complex.

The anthracycline agents useful in the invention may be selected from the group consisting of doxorubicin, daunorubicin, epirubicin, N-trifluoro-acetyl doxorubicin-14-valerate aclacinomycin, morpholinodoxorubicins, and derivatives thereof. Anthracycline compounds and derivatives thereof have tetracycline ring structures, with the cytotoxic agents of the class having quinone and hydroquinone moieties. Preferred for use in the invention are doxorubicin and derivatives thereof, particularly for the treatment of leukemias, lymphomas and other T-cell neoplasms.

The antibodies useful in a non-covalent immunocomplex of the present invention are antibodies, preferably monoclonal antibodies, which bind a target antigen and enhance the cytotoxicity of an anthracycline agent selected for use. Preferred for use in the invention, however, are monoclonal antibodies.

Monoclonal antibodies may be obtained by methods which are now well known in the art and need not be described in detail herein. See, Kohler, G. and Milstein, C., *Nature* 256:495–497 (1975). Briefly, however, these methods generally involve the immunization of a mouse or other suitable animal species with an immunogen, i.e., target antigen. After an immune response is generated, spleen cells of an immunized mouse having high serum titers against the target antigen, are fused with cells of an established myeloma tumor line using known techniques to form hybridomas producing monoclonal antibodies. Clones of hybridomas are thereafter screened by techniques well known in the art to select those antibodies having specificity for the target antigen.

Monoclonal antibodies having the desired specificity are further screened to select those which enhance the cytotoxicity of an anthracycline agent as an anti-tumor agent by formation of a non-covalent immunocomplex therewith. This may be accomplished by in vitro assays, such as those employing immunofluorescence labeling, to demonstrate the binding of an antibody-anthracycline complex to certain cells. Cytotoxicity assays may also be performed using well known techniques such as the inhibition of $^3$H-thymidine incorporation into cells.

The screening and selection of suitable monoclonal antibodies for use in the invention may further be accomplished by determining the in vivo effect of a non-covalent immunocomplex using animal models, such as immunocompromised mice with implanted tumors. Administration of an antibody-anthracycline complex to animal models and enhanced tumor regression, i.e., reduction of tumor diameter, provides an indication of the in vivo efficacy of such an immunocomplex. Accordingly, the use of animal tumor models provides a mechanism for screening an antibody-anthracycline complex to determine in vivo anti-tumor efficacy, as compared to the anthracycline agent administered alone, the antibody administered alone, as well as antibody conjugates of the anthracycline agent.

Preferred for use in the invention are monoclonal antibodies which bind a tumor-associated antigen. Among such antigens may be mentioned antigens associated with chronic lymphocytic leukemia, cutaneous T-cell lymphoma, or other T-cell neoplasms. Also preferred for use are monoclonal antibodies which bind tumor associated antigens which modulate the antibody, i.e. renders the antibody intracellular.

Particularly preferred for use in the invention is monoclonal antibody T101, an anti-human T-cell antibody. Monoclonal antibody T101, which binds a 65,000 molecular weight antigen associated with chronic lymphocytic leukemia, cutaneous T-cell lymphoma, and other T-cell neoplasms, has been previously described and characterized in Royston, I. et al., *Blood* 54 (Suppl 1):106A (1979), incorporated by reference herein.

In certain applications of the invention, it may be desirable to use a mixture of two or more monoclonal antibodies, antibody fragments such as Fab, Fab', F(ab')$_2$ fragments or any other fragment retaining the essential binding function of an antibody or mixtures thereof, or mixtures of whole antibody with antibody fragments.

Additionally, human monoclonal antibodies, produced by hybridomas which, for example, are the product of fusion of a human B-lymphocyte with an established mammalian lymphoid line, e.g., a human or mouse myeloma line, may be preferred in certain applications of the invention Chimeric monoclonal antibodies, comprising a variable region, i.e., binding region, and a constant region derived from different species by recombinant DNA techniques, e.g. a murine/human antibody, may also be preferred in certain applications of the invention. Chimeric antibodies which, for example, are the product of immunoglobulin genes comprising DNA segments encoding for a murine immunoglobulin variable region and DNA segments encoding for a human immunoglobulin constant region, may be less immunogenic than murine monoclonal antibodies. Methods for producing chimeric antibodies involve conventional recombinant DNA and gene transfection techniques well known in the art. See, Morrison, S. L. et al., *Proc. Nat'l. Acad. Sci.*, 81:6851 (1984).

Further, monoclonal antibodies which are characterized in the art as hybrid or bifunctional antibodies are desirable in certain applications of the invention. For example, hybrid antibodies having a dual specificity for different target antigens are preferred for use in the invention for the treatment of a heterogenous disease state. Hybrid or bifunctional antibodies may be derived either biologically, by cell fusion techniques, or chemically and may be comprised of whole antibodies and/or fragments thereof. Methods for obtaining such hybrid antibodies are described in the co-pending application of J. Martinis et al., Serial No. PCT/US83/00525, filed Apr. 12, 1983, and incorporated by reference herein.

Those skilled in the art will recognize that polyclonal antibodies may also be utilized in the invention. Polyclonal antibodies are obtained by well known techniques which involve stimulating an immune response against a target antigen in a suitable animal host such as a rabbit or other mammal. Chickens and other avian species may be used. Serum taken from the host is then subjected to affinity purification to isolate polyclonal antibodies against the target antigen. These antibodies are subsequently fractionated, if necessary, to isolate a subpopulation which binds the target antigen and enhances the cytotoxic efficacy of an athracycline agent in a non-covalent immunocomplex.

Further, those skilled in the art having the benefit of this disclosure will appreciate that the present invention suggests non-covalent immunocomplexes, other than an antibody-anthracycline complex provided herein, and their use in in vivo therapy to enhance the efficacy of other anti-tumor agents. For example, the invention suggests a composition comprising an immunocomplex of a substantially hydrophobic and lipophilic anti-tumor agent and an antibody selected to bind a target antigen and enhance the cytotoxocity of the agent. Preparation of such a complex, and selection of a suitable antibody for use therein, would be accomplished in the same manner as that described for an antibody-anthracycline complex of the invention.

The present invention is of substantial utility as it provides a means to enhance the efficacy of an anthracycline as an anti-tumor agent for use in in vivo therapy, particularly for chronic lymphocytic leukemia, cutaneous T-cell lymphoma and other T-cell neoplasms. Significant advantages are offered by the present invention in comparison to covalent antibody conjugates of anthracyclines. Specifically, as an anthracycline agent is not delivered to an in vivo target as an antibody conjugate, desired cytotoxic effects at the target tissue may be accomplished without the need for metabolic cleavage of the anthracycline agent from the antibody and the anthracycline agent may be more readily dissociated at the cell surface or intracellularly. Additionally, due to the small size of an antibody complex as compared to an antibody conjugate, the rate of clearance of the complex by the reticuloendothelial system is decreased. Further, as an antibody is not convalently conjugated with an anthracycline agent, antibody immunoreactivity, biodistribution, and metabolism will not be impaired. The utility of the present invention is further demonstrated by the following non-limiting example.

The antibody and anthracycline agent used in the example to demonstrate the enhanced efficacy of a non-covalent immunocomplex of the present invention were monoclonal antibody T101 and doxorubicin. Monoclonal antibody T101, an anti-human T-cell antibody, was selected for use in the example for purposes of illustration only. Those skilled in the art will appreciate that alternative monoclonal antibodies having the requisite anti-tumor specificity, such as monoclonal antibody T101, may be suitably utilized.

EXAMPLE I

T101-Doxorubicin Immunocomplex

Preparation of Monoclonal Antibody T101

Spleen cells obtained from mice hyperimmunized with a human T-cell line 8402 were fused to the mouse myeloma line NS-1. A hybridoma cell line was established which secreted a murine IgG2A monoclonal antibody specific for human T-lymphocytes, designated T101, and described in Royston, I. et al., Blood 54 (Suppl. 1): 106A (1979), incorporated by reference herein. Using indirect isotopic binding assays, T101 antibody binds to all human cells of thymic origin, including peripheral blood T-lymphocytes, thymus cells, and malignant T-cell leukemias and lymphomas. However, the antibody does not bind to non-T cells. T101 antibody precipitates a 65,000 molecular weight antigen on T-cells in the presence of complement.

Preparation of Non-Covalent T101-Doxorubicin Immunocomplex

Monoclonal antibody T101 was mixed with 1 and 10 equivalents of doxorubicin (Adriamycin ®, Adria Laboratories, Inc., Columbus, Ohio) ("DOX") per molecule of antibody in 100 mM NaHCO₃. The doxorubicin was previously dissolved in 50 mM phosphate buffer (pH 8.2). The antibody and doxorubicin mixture was allowed to stand for thirty minutes at room temperature after which time 193 μl of DMSO were added to the mixture. The DMSO and unbound doxorubicin were removed by dialysis against 0.1M NaHCO₃. The number of molecules of bound doxorubicin per molecule of antibody was determined using optical density measurements ($E_{480} = 1.14 \times 10^4$). The threshold for precipitation for the immunocomplexes described in this example, using doxorubicin non-covalently complexed to monoclonal antibody T101, was 5 drug molecules per antibody. Equilibrium dialysis, as shown in Table 1 below, and immunofluorescence assays were used to confirm the formation of T101-doxorubicin immunocomplex ("T101-DOX").

TABLE 1

| Time (Hrs.) | Inside Dialysis Membrane | | | Outside Dialysis | |
|---|---|---|---|---|---|
| | [DOX]* | [T101] | [DOX]/[T101] | Membrane [DOX] | [DOX] in/[DOX] out |
| 0 | 32.1 | 32.1 | 1.0 | 32.1 | 1 |
| 3.6 | 42.4 | 32.1 | 1.3 | 26.7 | 1.6 |
| 60** | 41.1 | 32.1 | 1.3 | 24.9 | 1.6 |

*Concentration units are M
**60 hour time point shows that equilibrium had been reached by 3.6 hours Preparation of T101-Doxorubicin-Dextran Immunoconjugate For purposes of comparison with the T101-doxorubicin immunocomplex, a covalent T101-doxorubicin-dextran immunoconjugate was prepared, as described by Hurwitz, E. et al., Int. J. Cancer, 21:747-755 (1978). Briefly, dextran was oxidized with periodate to form a polyaldehyde. The primary amine groups of doxorubicin and the T101 antibody acted as a Schiff base and bound to the aldehyde groups on the dextran. The preparation was then stabilized by reaction with sodium cyanoborohydride. It was estimated that 3.6-5.4 μg of doxorubicin were bound per 500 μg of T101 (i.e. 3 molecules of doxorubicin per molecule of T101).

Characterization of T101-Doxorubicin Immunocomplex

In Vitro Studies

For in vitro and cytotoxicity studies, Molt-4, T8402, and 8392 cell lines, were maintained as continuous cell suspensions in RPM 1-1640 media with 10% fetal calf serum (FCS). The Molt-4 cell line, and T8402 and 8392 cell lines are described in Minowada, J. et al., *J.N.C.I.,* 49:891–895 (1972), and Moore, G. et al, In Vitro 8:434 (1973), respectively. Molt-4 and T8402 are human T-cell leukemia lines with which T101 reacts, and 8392 is the B-cell antologous lymphoblastoid counterpart to T8402. Cells in log phase with viabilities exceeding 90% by trypan blue exclusion were used for these studies.

Immunofluorescence Assays

Indirect immunofluorescence assays were used to demonstrate the binding of T101, the T101-doxorubicin-dextran immunoconjugate and the non-covalent T101-DOX complex to cells. Aliquots of $10^6$ cells were incubated with the test reagent for 30 minutes with a fluorescein-conjugated, affinity-purified goat-mouse F(ab')$_2$. (Behringer-Mannheim, Indianapolis, Indiana). Direct binding of doxorubicin was determined using the direct red autofluorescence of the drug. Fluorescence analysis was performed on the Ortho Cytoflurograph-50H with 2100 H computer connection (Ortho, Westwood, Massachusetts). The nonspecific mouse IgG$_{2a}$ RPC5 (Litton Bionetics, Fredricksburg, Maryland) was used as a negative control for the indirect assays.

Cytotoxicity Assays

Inhibition of $^3$H-thymidine incorporation into cells was used as a measure of direct cellular cytotoxicity. Aliquots of $10^5$ cells/ml were incubated with various concentrations of the antibody-doxorubicin reagents for 15 minutes to 72 hours at 37° C. Following incubation, cells were washed free of antibody-doxorubicin reagent, resuspended in RPMI1640-10% FCS, then incubated with 0.25 $\mu$Ci of $^3$H-thymidine for 2 hours. Cells were then harvested using standard techniques and counts per minute (CPM) were measured in a liquid scintillation counter. Results were reported as the percent of control CPM by dividing test CPM by CPM from cells cultured with RPC5 or PBS, and multiplying the quotient by 100.

Figure 1B:
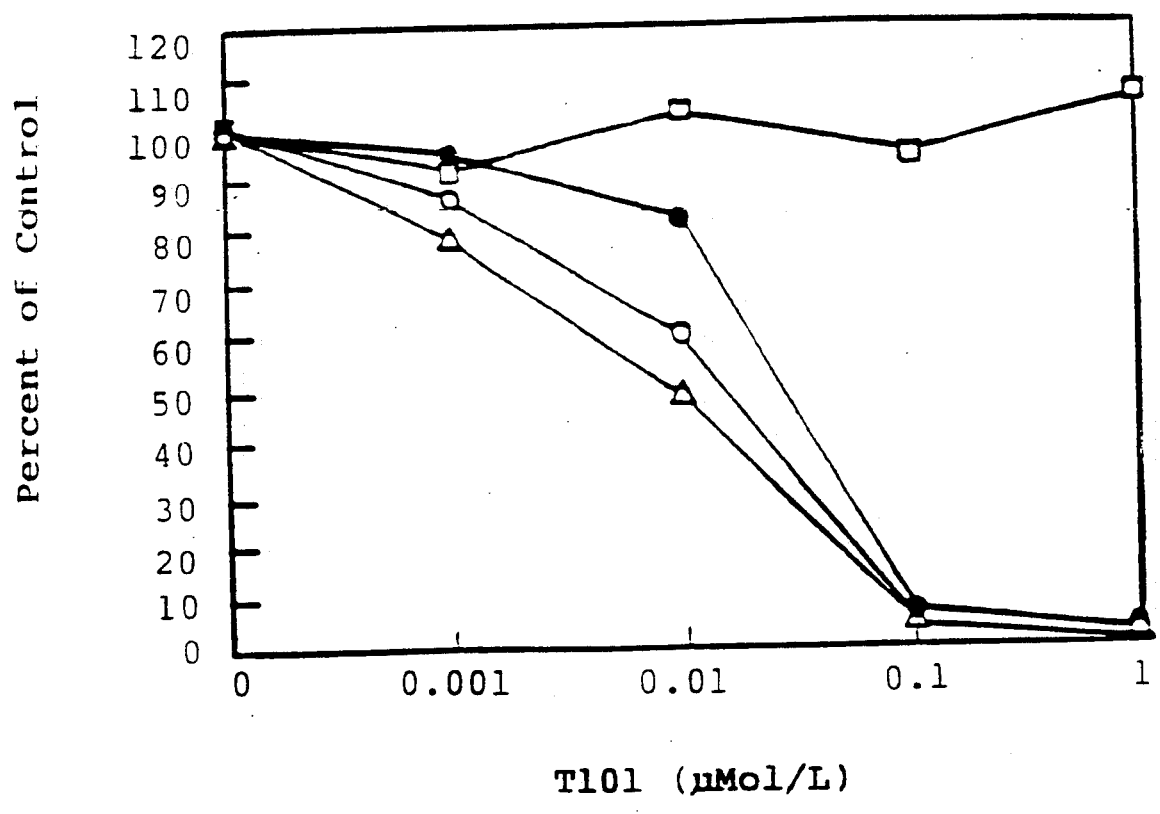
Figure 1C:
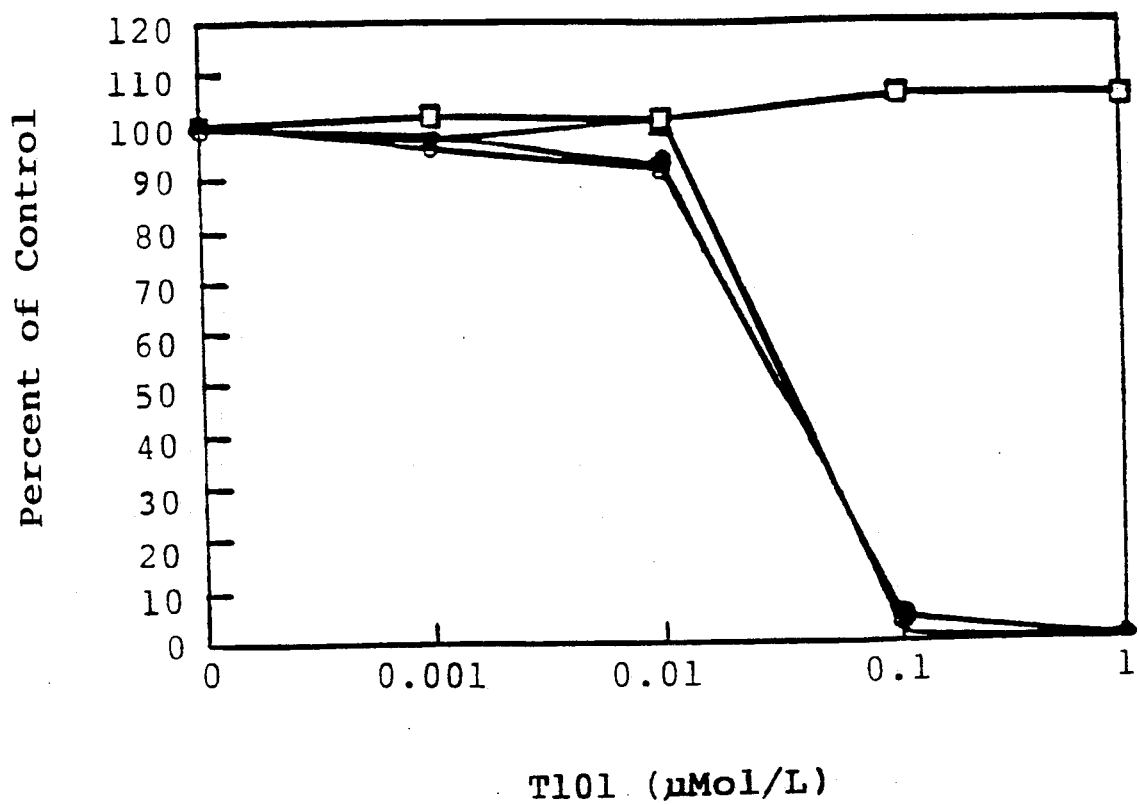

FIG. 1 shows the results of $^3$H-TdR uptake in the presence of free T101, free doxorubicin, the T101-doxorubicin-dextran immunoconjugate and the T101-DOX immunocomplex. More specifically, FIG. 1 shows the inhibition of $^3$H thymidine uptake in 8402 T cells (FIG. 1A), 8293 B cells (FIG. 1B) and MOLT-4 T cells (FIG. 1C) in the presence of various molar concentrations of DOX, or the amount of T101 associated with that concentration of DOX in the T101-DOX-dextran immunoconjugate. Graphs are for T101 alone in concentrations equivalent to the amount of T101 in the immunoconjugate, DOX alone in the same concentration as contained in the immunoconjugate, the T101-DOX-dextran immunoconjugate, and T101 plus DOX in the same concentrations as in the immunoconjugate. Similar values were seen for all DOX arms regardless of cell line. As indicated by FIG. 1, the $^3$H-TdR uptake was comparable for all doxorubicin containing reagents.

In Vivo Animal Tumor Studies

For in vivo studies, 3.6 $\mu$g of doxorubicin was mixed with 500 $\mu$g of monoclonal antibody T101. Albumin was present in this preparation and is known to form complexes in vitro with the drug.

In vivo animal tumor studies were carried out using athymic mice bearing palpable, measurable subcutaneous tumors of the Molt-4 cell line. The reproducibility of tumor establishment, and stability of the T65 antigen in this system have been previously established. See, Dilman, R. et al., *Cancer Res.* 45:5632–5636 (1985). Briefly, 5–6 week old female Balb/c Nu/Nu mice were irradiated with 200 cGy once a week for 3 weeks, then injected subcutaneously with $10^7$ culture Molt-4 cells and $10^7$-irradiated HT1080 fibrosarcoma cells. Animals were examined 10–14 days later for presence of palpable, measurable tumors, and then distributed among various treatment arms so that the sum of cross-sectional diameters of the measured tumors were approximately equal in all groups.

Chemotherapy

There were six therapeutic arms in the animal trial, and two schedules of administration. The two schedules involved a single intraperitoneal (IP) injection or five daily IP injections. The six therapeutic arms included: (1) a control group which received doxorubicin and a non-specific murine IgG2A, designated UPC; (2) a group which received 500 $\mu$g injections of T101; (3) a group which received 3.6 $\mu$g doxorubicin; (4) a group which received injections of the T101-DOX-dextran immunoconjugate which contained 500 $\mu$g T101 and 3.6 $\mu$g doxorubicin; (5) a group which received separate IP injections of T101 and doxorubicin; and (6) a group which received injections of the non-covalent T101-DOX immunocomplex consisting of 500 $\mu$g of T101 and 3.6 $\mu$g doxorubicin.

All animals had palpable, measurable subcutaneous tumors at the time therapy was started. Cross-sectional diameters were measured using Mitutoya calipers (Fisher Scientific, Irvine, California). Measurements were obtained on three separate occasions on the day of treatment, and every 3–4 days thereafter. The means of each day's three tumor measurements was recorded as the cross-sectional diameter of the tumor. Animals were observed daily for general well-being and survival. All surviving animals were sacrificed 21 days after the start of therapy. All animals tolerated the injections without any apparent acute or delayed toxicities.

For purposes of analysis, a tumor which totally disappeared following therapy was considered a complete regression, and any significant descrese in tumor size was considered a partial regression. For tumor-response curve analysis, the cross-sectional diameters for all tumors of all animals in each subgroup were averaged and the mean plotted versus the number of days after start of therapy.

Figure 2A:
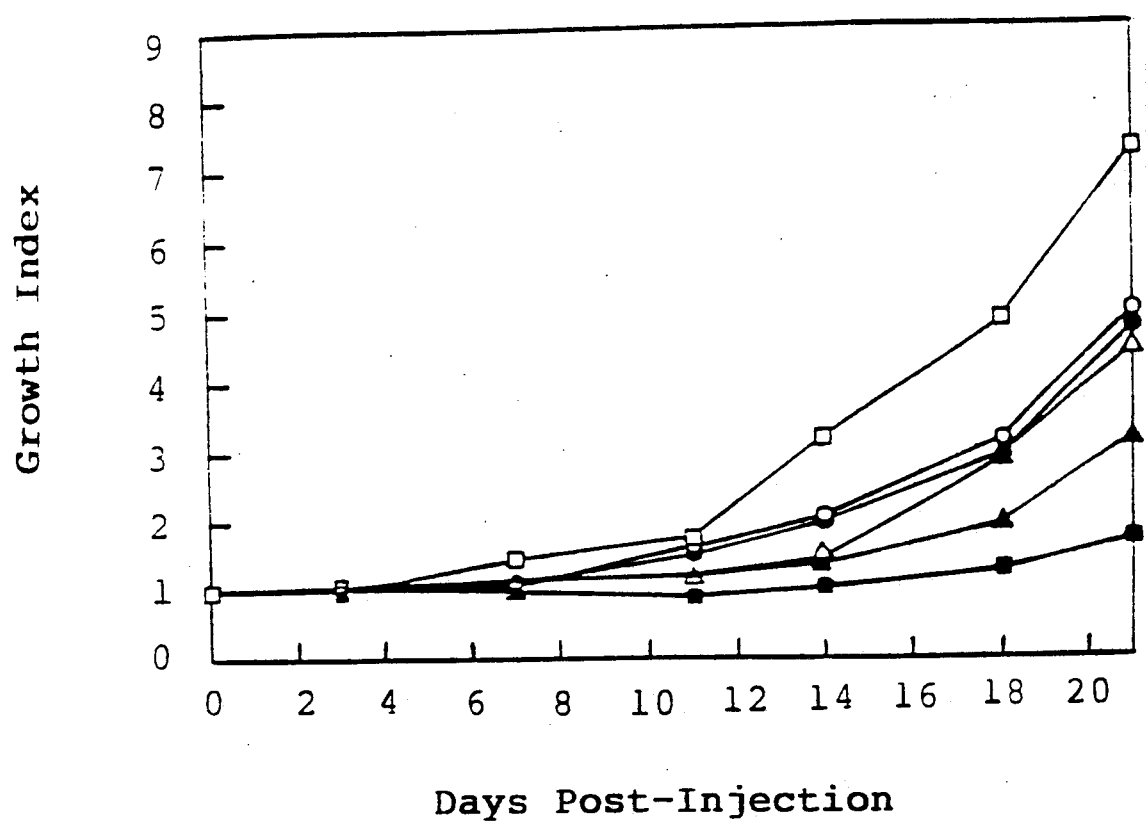
FIG. 2(A–C) shows the tumor growth curves for treatments in animal models using antibody alone, doxorubicin alone, antibody conjugates, the T101-DOX immunocomplex of the invention, and a control.
Figure 2B:
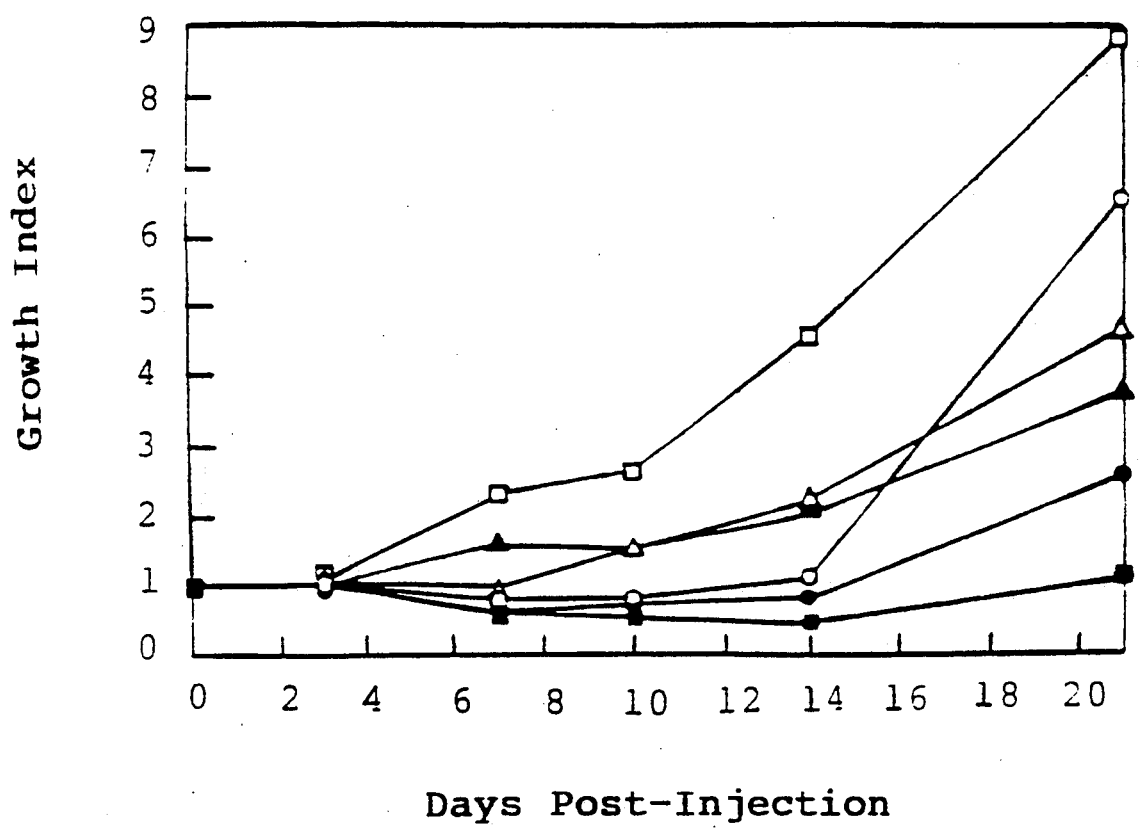
Figure 2C:
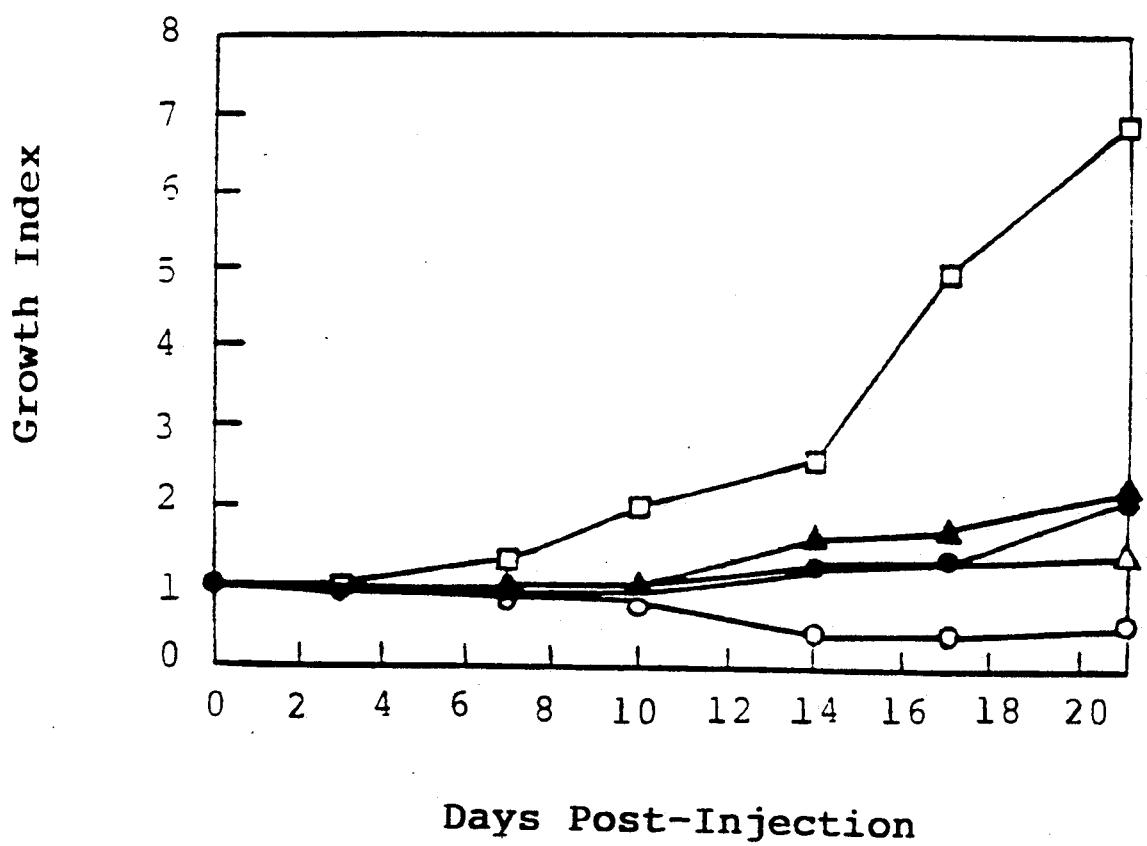

FIG. 2 shows the tumor growth curves for the various treatment conditions in the animal models following either a single injection or 5 multiple injections of a reagent. More particularly, FIGS. 2A and 2B show the growth curves of MOLT-4 tumors growing in anthymic mice expressed as an index equal to the ratio of the product of tumor cross-sectional diameters at various time points and the product of tumor cross-sectional diameters immediately prior to initiation of treatment. Means for 12–15 tumors were plotted for each treatment. All tumors were 20–30 mm² in size at the time of treatment. FIG. 2A shows growth curves following a single i.p. injection, and FIG. 2B shows curves following five days of i.p. injections. Both FIGS. 2A and 2B include non-specific antibody as a control , T101 alone , DOX alone , T101 and DOX injected separately, i.p. , T101 and DOX mixed in the syringe prior to i.p. injection , and T-101-DOX-dextran immunoconjugate . FIG. 2C shows growth curves of MOLT-4 tumors growing in athymic mice, expressed as an index of the product of tumor cross-sectional diameters at each point in time divided by the product of crosssectionl diameters prior to treatment. Means for 12 tumors were plotted for each treatment. All tumors were 20–30 mm² in size when therapy was initiated. Includes in the experiment summarized in FIG. 2C were single i.p. injections of nonspecific antibody UPC as the control , T101 alone , DOX alone , nonspecific antibody mixed with DOX , and T101 mixed with DOX . In the single injection group, the only treatment which resulted in regression of palpable tumor was the non-covalent T101-DOX immunocomplex. In the multiple injection group there was some regression of tumor in all the doxorubicin treated arms, but the T101-DOX immunocomplex again produced the most sustained antitumor effect.

Tables 2 and 3 demonstrate the efficacy of the various therapies in terms of complete or partial tumor regression. The best results were obtained with the non-covalent T101-DOX immunocomplex with 27% of tumors completely regressing following a single injection, and 73% completely regressing following five daily injections. When the results of both treatment schedules were combined, there was a 46% complete regression rate for the T101-DOX complex versus 13–18% for T101 or any of the other doxorubicin-containing reagents.

TABLE 2

| Treatment | Multiple Injections | | | Single Injections | | |
|---|---|---|---|---|---|---|
| | mice | w/ CR | w/ PR | mice | w/ CR | w/ PR |
| Control | 14 | 0 | 0 | 13 | 0 | 1 |
| T101 | 15 | 1 | 0 | 15 | 2 | 0 |
| T101-DOX-dextran | 15 | 1 | 2 | 14 | 5 | 3 |
| DOX | 15 | 1 | 0 | 14 | 1 | 2 |
| T101 + DOX* | 12 | 0 | 0 | 11 | 3 | 5 |
| T101-DOX-complex** | 15 | 4 | 4 | 14 | 11 | 1 |

*T101 + DOX injected separately i.p.
**T101 + DOX drawn into same syringe, then injected

TABLE 3

| Treatment | Mice | CR | PR |
|---|---|---|---|
| UPC10 | 12 | 0 | 0 |
| T101 | 12 | 0 | 2 |
| DOX | 12 | 0 | 2 |
| UPC10 + DOX* | 12 | 0 | 1 |
| T101 + DOX* | 12 | 7 | 3 |

*Both premixed in syringe, then injected i.p.

Accordingly, the above results show that: (1) non-covalent complexation of a murine monoclonal antibody with an anthracycline agent results in a stable immunocomplex for in vivo therapy; (2) the non-covalent immunocomplex produces tumor regressions in an athymic mouse model of human T-cell malignancy; (3) small complexes, such as the complexed T101-DOX immunocomplex, produce a greater anti-tumor effect than a larger T101-DOX-dextran immunoconjugate with a comparable number of doxorubicin molecules attached, and has a greater anti-tumor effect than T101 alone, doxorubicin alone in equivalent doses, and T101 and doxorubicin injected separately into the same animal; (4) the anti-tumor effect of non-covalent immunocomplexes is specifically associated with the specificity of the antibody for the tumor target, e.g. T101. (5) difficulty in demonstrating cytotoxic specificity in vitro does not preclude successful in vivo use of such immunocomplexes because of factors which may facilitate drug binding to cells by other than the antibody portion of the complex.

The ability to produce tumor regressions in animal models is of importance to establish a rationale for clinical studies with such immunocomplexes. There are innumerable possible antibody-anthracycline immunocomplexes; the athymic mouse tumor model, as used herein, provides a system for screening and selecting said immunocomplexes on the basis of anti-tumor efficacy against human tumors Analysis of the experiments described herein established that the non-covalent T101-DOX-immunocomplex produced enhanced anti-tumor effect with no apparent toxicity, and that this preparation was clearly superior to the T101-DOX-dextran immunoconjugate, the combination of T101 and doxorubicin injected separately, and the control.

The results described herein, beyond demonstrating the feasibility of the specifically exemplified non-covalent immunocomplex comprising monoclonal antibody T101 and doxorubicin, provide a basis for the applicability of the present invention to alternative immunocomplexes comprising monoclonal antibodies having anti-tumor specificity and anthracycline agents.

Although, the foregoing description of the invention has been directed to particular applications for purposes of illustration and explanation, it will be apparent to those skilled in the art that modifications and changes will be possible without departing from the spirit and the scope of the invention. It is intended that the following claims be interpreted to embrace all such modifications.

We claim:

1. A composition for treating in vivo a disorder associated with chronic lymphocytic leukemia, cutaneous T-cell lymphoma, or other human T-cell neoplasm, comprising a non-covalent immunocomplex of an anthracycline agent and a monoclonal antibody or antigen-recognizing fragment thereof, said anthracycline agent is selected from the group consisting of doxorubicin, doxorubicin-14-valerate, morpholinodoxorubicin and derivatives thereof, and said antibody or antibody fragment being selected to bind an antigen recognized by a T101 antibody and enhance the in vivo cytotoxicity of said agent.

2. The composition according to claim 1 wherein said anthracycline agent is doxorubicin.

3. The composition according to claim 1 wherein said antibody binds a tumor-associated antigen.

4. The composition according to claim 3 wherein said antibody binds a tumor-associated antigen which modulates said antibody.

5. The composition according to claim 3 wherein said antibody is monoclonal antibody T101.

6. The composition of claim 1 in which the monoclonal antibody or fragment thereof is a chimeric antibody, or antigen-recognizing fragment thereof.

7. The composition of claim 1 in which the monoclonal antibody or fragment thereof is a bifunctional antibody, or antigen-recognizing fragment thereof.

8. A method for treating in vivo a disorder associated with chronic lymphocytic leukemia, cutaneous T-cell lymphoma, or other human T-cell neoplasm which comprises administering to a patient in need thereof a therapeutically-effective amount of a composition comprising a non-covalent immunocomplex of an anthracycline agent and a monoclonal antibody or antigen-recognizing fragment thereof, said anthracycline agent is selected from the group consisting of doxorubicin, doxorubicin-14-valerate, morpholinodoxorubicin and derivatives thereof, and said antibody or fragment being selected to bind an antigen recognized by a T101 antibody and enhance the in vivo cytotoxicity of said agent.

9. The method according to claim 8 wherein said anthracycline agent is doxorubicin.

10. The method according to claim 8 wherein said monoclonal antibody binds a tumor-associated antigen.

11. The method according to claim 10 wherein said antibody binds a tumor-associated antigen which modulates said antibody.

12. The method according to claim 8 wherein said antibody is monoclonal antibody T101.

13. The method of claim 8 in which the monoclonal antibody or fragment thereof is a chimeric antibody, or antigen-recognizing fragment thereof.

14. The method of claim 8 in which the monoclonal antibody or fragment thereof is a bifunctional antibody, or antigen-recognizing fragment thereof.

* * * * *